United States Patent
Pinkos et al.

(10) Patent No.: US 9,045,382 B2
(45) Date of Patent: Jun. 2, 2015

(54) PROCESS FOR WORKING UP SOLVENT-CONTAINING HYDROGENATION PRODUCT MIXTURES

(75) Inventors: Rolf Pinkos, Bad Duerkheim (DE); Jens Heimann, Worms (DE); Hans-Martin Polka, Weinheim (DE); Heiko Urtel, Mannheim (DE); Gunther Windecker, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 387 days.

(21) Appl. No.: 12/307,367

(22) PCT Filed: Jul. 16, 2007

(86) PCT No.: PCT/EP2007/057325
§ 371 (c)(1),
(2), (4) Date: Jan. 5, 2009

(87) PCT Pub. No.: WO2008/012229
PCT Pub. Date: Jan. 31, 2008

(65) Prior Publication Data
US 2009/0314992 A1    Dec. 24, 2009

(30) Foreign Application Priority Data
Jul. 25, 2006 (EP) .................................... 06117797

(51) Int. Cl.
*C07C 27/26* (2006.01)
*C07C 29/14* (2006.01)
*C07C 29/16* (2006.01)
*C07B 63/00* (2006.01)
*C07C 29/149* (2006.01)
*C07C 29/86* (2006.01)
*C07C 209/48* (2006.01)

(52) U.S. Cl.
CPC ............... *C07B 63/00* (2013.01); *C07C 29/149* (2013.01); *C07C 29/86* (2013.01); *C07C 209/48* (2013.01)

(58) Field of Classification Search
CPC ...... C07C 29/141; C07C 31/20; C07C 29/80; F16F 1/34; C10G 45/09; C10G 1/08; B01J 19/00
USPC .......... 252/364; 568/856, 881, 835, 861, 863, 568/880, 882, 883
See application file for complete search history.

(56) References Cited

U.S. PATENT DOCUMENTS

| | | | |
|---|---|---|---|
| 1,565,719 A * | 12/1925 | Dunkley .......................... | 180/11 |
| 4,254,059 A | 3/1981 | Grey et al. | |
| 5,093,535 A * | 3/1992 | Harrison et al. .............. | 568/881 |
| 6,265,596 B1 | 7/2001 | Haerroed et al. | |
| 2007/0027345 A1 | 2/2007 | Hugo et al. | |
| 2007/0088178 A1 | 4/2007 | Hugo et al. | |
| 2008/0242897 A1 * | 10/2008 | Lorenz et al. .................. | 568/856 |

FOREIGN PATENT DOCUMENTS

| | | |
|---|---|---|
| DE | 25 19 817 | 11/1976 |
| DE | 103 41 612 | 4/2005 |
| EP | 0 285 420 A1 | 10/1988 |
| EP | 1016622 * | 7/2000 |
| EP | 1 477 219 A1 | 11/2004 |
| GB | 1565719 * | 12/1977 |
| GB | 1 551 741 | 8/1979 |
| GB | 1 565 719 | 4/1980 |
| JP | 53-84907 | 7/1978 |
| JP | 4 338346 | 11/1992 |
| WO | WO 2005/026102 A1 | 3/2005 |

OTHER PUBLICATIONS

Japanese Office Action Issued Jan. 11, 2013 in Patent Application No. 2009-521212 (English translation only).

* cited by examiner

*Primary Examiner* — Monique Peets
(74) *Attorney, Agent, or Firm* — Oblon, McClelland, Maier & Neustadt, L.L.P.

(57) ABSTRACT

The present invention relates to a process for separating off solvents from solvent-comprising hydrogenation outputs from a catalytic hydrogenation process, which comprise at least one water-soluble hydrogenation product having at least one alcohol, lactone, ether, lactam or amino group in a solvent which is immiscible or not completely miscible with water and has a boiling point below 100° C., wherein water is added to the hydrogenation output, the solvent-comprising phase is separated off and recirculated to the hydrogenation.

37 Claims, No Drawings

PROCESS FOR WORKING UP SOLVENT-CONTAINING HYDROGENATION PRODUCT MIXTURES

The present invention relates to a process for separating off solvents from solvent-comprising hydrogenation outputs from catalytic hydrogenations using hydrogen-comprising gases, which comprise at least one water-soluble hydrogenation product having at least one alcohol, lactone, ether, lactam or amino group in a solvent which is immiscible or not completely miscible with water and has a boiling point below 100° C., wherein water is added to the hydrogenation output, the solvent-comprising phase is separated off and recirculated to the hydrogenation.

Catalytic hydrogenation by means of hydrogen is a widely used process in chemistry. If the compounds being hydrogenated form water-soluble hydrogenation products, the hydrogenation is usually carried out without solvents. Examples of compounds which are important in industrial organic chemistry and whose hydrogenations can be carried out in the gas phase or liquid phase to form water-soluble compounds are, for example, carbon monoxide, esters, acids, lactones, anhydrides, aldehydes, ketones, nitriles, amides and amino acids. Since the reaction rates under these conditions are low, space-time yields of less than 1 kg of product/liter of reaction volume×h are achieved.

However, hydrogenation processes for water-soluble compounds in which the reaction rate and thus the space-time yield has been able to be increased greatly so that the reaction volume, which is expensive in industrial applications, and the required amount of catalyst can be significantly reduced are known, for example, from U.S. Pat. No. 6,265,596.

In these processes, the hydrogenation is carried out under superatmospheric pressure in the presence of solvents having a low boiling point and the reaction mixture is depressurized, usually to atmospheric pressure, to isolate the product. Recirculation of the solvent, especially when the hydrogenation is carried out at high pressures, is problematical, so that the advantage of the low reaction volume and the small amount of catalyst required can be balanced out again.

After the hydrogenation, the hydrogenation output, which comprises excess hydrogen, product, any intermediates and by-products formed, unreacted starting material and the solvent if the hydrogenation has been carried out in the presence of a solvent are generally cooled and depressurized before further work-up steps. Here, hydrogen and any solvent are obtained in gaseous form. If the solvent is liquid under the process conditions of the hydrogen separation, it is separated together with the product mixture, usually by distillation. The solvent is then obtained as low boiler, either in liquid or gaseous form.

The recovered solvent can either be discarded or, as is preferred in industrial processes in which economic considerations are of key importance, recirculated. However, recirculation of the solvent firstly requires the expenditure of considerable amounts of compression energy.

Since the hydrogenation is carried out at high pressures, the solvent has to be compressed from a low pressure level back to the reaction pressure. Particularly in the case of solvents which are normally gaseous at ambient temperature, this is energy-consuming and therefore economically disadvantageous. In addition, it is necessary to bring the recirculated components solvent and hydrogen back to the starting temperature level required for the hydrogenation, which is again energy-consuming.

It is therefore an object of the present invention to provide a process which makes effective separation of the solvent from solvent-comprising hydrogenation outputs which are obtained from catalytic hydrogenation and comprise water-soluble hydrogenation products possible. The separation should be so effective that the circulation of the solvent to the hydrogenation is economical.

We have now surprisingly found a process for separating off solvents from solvent-comprising hydrogenation outputs from catalytic hydrogenations using hydrogen-comprising gases, which comprise at least one water-soluble hydrogenation product having at least one alcohol, lactone, ether, lactam or amino group in a solvent which is immiscible or not completely miscible with water and has a boiling point below 100° C., wherein water is added to the hydrogenation output, the solvent-comprising phase is separated off and recirculated to the hydrogenation.

For the purposes of the present invention, a hydrogenation output is the reaction mixture taken from the hydrogenation reactor after the hydrogenation without further work-up steps such as distillations. The hydrogenation output comprises the solvent and the hydrogenation product and also possibly excess hydrogen, any intermediate and by-products formed and unreacted starting material. In the present patent application, the hydrogenation product is the water-soluble target product to be produced by the hydrogenation or a mixture of a plurality of target products. Water-soluble hydrogenation products in the context of the present patent application are, for example, methanol, ethanol, propanol, butanol, isobutanol, ethylene glycol, 1,2-propylene glycol and 1,3-butanediol, 1,4-butanediol, 1,2,4-butanetriol, tetrahydrofuran, 2-methyltetrahydrofuran, 3-methyltetrahydrofuran, optionally methyl-substituted gamma-butyrolactone, 1,5-pentanediol, 1,6-hexanediol, 1,4-pentanediol, 2,5-bis(hydroxymethyl)tetrahydrofuran, 1,12-dodecanediol, pyrrolidone, N-alkylpyrrolidones, C-alkylated pyrrolidones, C- and N-alkylated pyrrolidones, N-alkylated monoamines and diamines and amino alcohols and mixtures thereof. Preferred water-soluble hydrogenation products are 1,4-butanediol, tetrahydrofuran, gamma-butyrolactone, 1,5-pentanediol, 1,6-hexanediol, 1,4-pentanediol, 2,5-bis(hydroxymethyl)tetrahydrofuran, pyrrolidone, N-alkylpyrrolidones, C-alkylated pyrrolidones, C- and N-alkylated pyrrolidones, and also amino alcohols or mixtures thereof.

The products formed by the process of the invention are, for example, sought-after solvents such as tetrahydrofuran or starting materials for polyesters, e.g. 1,4-butanediol or 1,6-hexanediol.

Solvents which can be used according to the invention are solvents which are immiscible or not completely miscible with water under the pressure and temperature conditions of the process of the invention and have a boiling point at a pressure of 1 bar below 100° C., preferably below 70° C., particularly preferably below 50° C., very particularly preferably below 25° C.

The weight ratio of solvent to hydrogenation product in the hydrogenation output is in the range from 0.1 to 1000, preferably from 0.5 to 100, particularly preferably from 1 to 50.

Examples of solvents which can be used according to the invention are carbon dioxide, argon, nitrogen, hydrocarbons such as methane, ethane, propane, butane, isobutane, pentane and its isomers, cyclopentane, hexane and its isomers, cyclohexane, heptane and its isomers, aromatics such as benzene, toluene, ethers such as dimethyl ether, methyl ethyl ether, diethyl ether, dibutyl ether, methyl propyl ether, methyl isopropyl ether, ethyl propyl ether, ethyl isopropyl ether, dibutyl ether, methyl tert-butyl ether, methyl n-butyl or isobutyl ether, ethyl n-butyl or isobutyl ether, propyl n-butyl or isobutyl ether, isopropyl n-butyl or isobutyl ether. The abovementioned solvents can be perfluorinated or partially fluorinated. Preference is given to hydrocarbons having from 1 to 6 carbon atoms, dialkyl ethers having up to 8 carbon atoms, particularly preferably propane, butane, pentane, dimethyl ether, diethyl ether and methyl-tert-butyl ether, and also carbon dioxide as solvents for the process of the invention.

An amount of water which effects phase separation is added to the hydrogenation output; if slight phase separation occurs without addition of water, an amount of water which results in complete phase separation is added. This amount of water is from 0.01 to 1000% by weight of water, preferably from 50 to 300% by weight of water, particularly preferably from 100 to 200% by weight of water, in each case based on the hydrogenation output.

During the phase separation according to the invention, the pressure is at a value corresponding to the pressure of the preceding hydrogenation or up to 50 bar lower. The pressure of the phase separation is preferably from 10 to 400 bar, preferably from 50 to 350 bar and particularly preferably from 75 to 300 bar. In a particularly preferred embodiment of the process, the pressure in the phase separation is at or up to 20 bar below the pressure of the preceding hydrogenation.

The phase separation can be carried out at the temperature prevailing at the hydrogenation reactor output of the hydrogenation preceding the process of the invention or at a lower temperature, preferably at from 5 to 250° C. lower. The hydrogenation output is particularly preferably cooled to the temperature prevailing at the outlet of the hydrogenation reactor for the phase separation. The phase separation according to the invention is carried out in apparatuses known per se for this purpose, e.g. phase separators or decanters.

While the aqueous phase comprises predominantly the hydrogenation product, the phase comprising the solvent (solvent phase) comprises not only the solvent and hydrogen but also any unreacted hydrogenation starting material, intermediates of the hydrogenation, small amounts of the hydrogenation product and by-products of the hydrogenation.

The work-up of the aqueous phase comprising the hydrogenation product is effected by methods known per se, for example by crystallization and/or distillation. In general, at least the water is separated off from the hydrogenation product by distillation. The distillation conditions here are advantageously selected so that, as a result of the pressure and temperature conditions selected for the phase separation, either water or the hydrogenation product vaporizes on entry into the distillation column. The water separated off is preferably recirculated to the phase separation.

The phase separation according to the invention can be carried out continuously or batchwise together with a preceding hydrogenation, with the continuous mode of operation being preferred.

In a preferred embodiment, the solvent separated off is recirculated without work-up to the hydrogenation. Preference is given to the starting material for the hydrogenation being mixed completely or at least virtually completely with this solvent before it reaches the catalyst.

Hydrogen-comprising gases which are suitable for the process of the invention are hydrogen and also its mixtures with further gases which are inert under the reaction conditions, for example nitrogen. Preference is given to using hydrogen.

The hydrogenation is preferably carried out over heterogeneous catalysts which are particularly preferably fixed in place in the reactor. As catalysts in the hydrogenation process, it is possible to use ones which comprise at least one of the following elements as metal and/or as compound, for example as oxide: Fe, Cu, Ag, Au, Ni, Pd, Pt, Co, Rh, Ir, Ru, Mn, Re, Cr or Mo. The catalyst preferably comprises Fe, Cu, Co, Re, Ni, Ru, Pt or Pd.

A suitable catalyst is, in particular, at least one heterogeneous catalyst, with at least one of the abovementioned metals (active metals) being able to be used as metal either as such, as Raney catalyst and/or applied to a customary support. If two or more active metals are used, these can be present either separately or as an alloy. It is possible to use at least one metal as such and at least one other metal as Raney catalyst or at least one metal as such and at least one other metal applied to at least one support, or at least one metal as Raney catalyst and at least one other metal applied to at least one support or at least one metal as such and at least one other metal as Raney catalyst and at least one other metal applied to at least one support.

The catalysts used can, for example, also be precipitated catalysts. Such catalysts can be produced by precipitating their catalytically active components from their salt solutions, in particular from the solutions of their nitrates and/or acetates, for example by addition of solutions of alkali metal and/or alkaline earth metal hydroxide and/or carbonate, for example as sparingly soluble hydroxides, hydrated oxides, basic salts or carbonates, subsequently drying the precipitates obtained and then converting these by calcinating at generally from 300 to 700° C., in particular from 400 to 600° C., into the corresponding oxides, mixed oxides and/or mixed-valence oxides which are reduced to the respective metals and/or oxidic compounds of a lower oxidation state and converted into the actual catalytically active form by treatment with hydrogen or hydrogen-comprising gases in the range of generally from 50 to 700° C., in particular from 100 to 400° C. Here, the reduction is generally carried out until no more water is formed. In the production of precipitated catalysts which comprise a support material, the precipitation of the catalytically active components can be carried out in the presence of the respective support material. The catalytically active components can advantageously be precipitated simultaneously with the support material from the appropriate salt solutions.

Preference is given to using hydrogenation catalysts which comprise the metals or metal compounds which catalyze the hydrogenation deposited on a support material.

Apart from the abovementioned precipitated catalysts which comprise a support material in addition to the catalytically active components, the process of the invention can generally also be carried out using support materials in which the catalytically hydrogenation-active component has been applied to a support material by, for example, impregnation.

The way in which the catalytically active metal is applied to the support is generally not critical and the application can be brought about in a variety of ways. The catalytically active metals can be applied to these support materials by, for example, impregnation with solutions or suspensions of the salts or oxides of the respective elements, drying and subsequent reduction of the metal compounds to the corresponding metals or compounds having a lower oxidation state by means of a reducing agent, preferably by means of hydrogen or complex hydrides. Another possible way of applying the catalytically active metals to these supports is to impregnate the supports with solutions of salts which are readily decomposed thermally, for example nitrates, or complexes which are easily decomposed thermally, for example carbonyl or hydrido complexes of the catalytically active metals, and to heat the support which has been impregnated in this way to temperatures in the range from 300 to 600° C. to bring about thermal decomposition of the adsorbed metal compounds.

This thermal decomposition is preferably carried out under a protective gas atmosphere. Suitable protective gases are, for example, nitrogen, carbon dioxide, hydrogen or noble gases. Furthermore, the catalytically active metals can be deposited on the catalyst support by vapor deposition or by flame spraying. The content of catalytically active metals in these supported catalysts is in principle not critical for the success of the process of the invention. In general, higher contents of catalytically active metals in these supported catalysts lead to higher space-time conversions than do lower contents. In general, supported catalysts whose content of catalytically active metals is in the range from 0.01 to 90% by weight, preferably in the range from 0.1 to 40% by weight, based on the total weight of the catalyst, are used. Since these contents relate to the total catalyst including support material but the various support materials have very different specific gravities and specific surface areas, it is also conceivable for the contents to be below or above these figures without this having an adverse effect on the result of the process of the invention. Of course, a plurality of catalytically active metals can also be applied to the respective support material. Furthermore, the catalytically active metals can, for example, be applied to the support by the method of DE-A 25 19 817, EP-A 1 477 219 A1 or EP-A 0 285 420 A1. In the catalysts according to the above-mentioned documents, the catalytically active metals are present as alloys which are produced by thermal treatment and/or reduction of the, for example, by impregnation of the support material with a salt or complex of the abovementioned metals.

Owing to the toxicity of chromium-comprising catalysts, preference is given to using chromium-free catalysts. Of course, corresponding chromium-comprising catalysts known to those skilled in the art are technically also suitable for use in the process of the invention, but the desired advantages which, in particular, relate to environmental and occupational hygiene issues will not be obtained.

The activation of both the precipitated catalysts and the supported catalysts can also be carried out in situ at the beginning of the reaction by means of the hydrogen which is present. Preference is given to activating these catalysts separately before use.

As support materials both for precipitated catalysts and for supported catalysts, it is possible to use the oxides of aluminum and titanium, zirconium dioxide, silicon dioxide, clay minerals such as montmorillonites, bentonites, silicates such as magnesium silicates or aluminum silicates, zeolites such as those of the structure types ZSM-5 or ZSM-10, or activated carbon. Preferred support materials are aluminum oxides, titanium dioxides, silicon dioxide, zirconium dioxide and activated carbon. Of course, mixtures of various support materials can also serve as support for catalysts which can be used in the process of the invention. Metallic supports on which the hydrogenation-active metal has been deposited, for example Cu on which, for example, Pd, Pt or Ru has been deposited from the corresponding metal salts dissolved in water, are also suitable.

Particularly preferred catalysts to be used according to the invention are supported catalysts which comprise Fe, Cu, Co, Re; Ni, Pt and/or Pd, or with a special preference being given to activated carbon, aluminum oxide, titanium dioxide and/or silicon dioxide or mixtures thereof as supports.

A heterogeneous catalyst which can be used according to the invention is preferably used as a fixed-bed catalyst in the hydrogenation stage according to the invention, and the catalysts are preferably used in the form of pieces, i.e. as shaped bodies in the form of, for example, crushed material, rings, pellets or extradates. The diameters of the individual shaped catalyst bodies are in the range from 0.01 to 15 mm, preferably from 0.02 to 10 mm, particularly preferably from 0.05 to 5 mm.

The hydrogenation of the invention can be carried out batchwise or continuously, e.g. in one or more reactor tubes filled with a catalyst dent, with the continuous mode of operation being preferred. The hydrogenation according to the invention is particularly preferably operated continuously together with the phase separation according to the invention as a total process.

The hydrogenation is carried out at a pressure and temperature level which corresponds at least to that of the phase separation. The reference point for pressure and temperature here is the reactor outlet. For example, the hydrogenation pressures are in the range from 10 to 400 bar, preferably from 50 to 350 bar and particularly preferably from 75 to 300 bar. The temperature in the hydrogenation is from 20 to 370° C., preferably from 40 to 350° C. and particularly preferably from 70 to 330° C.

The process of the invention is illustrated but not restricted by the following examples.

EXAMPLES

Example 1

An oil-heated double-walled tube reactor (3 cm internal diameter) was charged with 3 ml of a Cu catalyst (60% of CuO, 30% of $Al_2O_3$, 10% of $Mn_2O_3$) in the form of 0.1 mm shaped bodies. The catalyst was activated firstly using nitrogen/hydrogen mixtures, later using pure hydrogen, at 250° C. and 250 bar. At 250° C. and 250 bar, 20 g/h of dimethyl adipate, 180 g/h of dimethyl ether and 10 mol of hydrogen per mol of starting material were pumped via a heated helical tube over the catalyst.

The hydrogenation output had a temperature of 270° C. and traveled via a cooled mixing section upstream of which 100 g/h of water (25° C.) were introduced to a phase separator having a volume of 2 l. The temperature in the phase separator was 50° C. and the pressure was 250 bar. At a fill level of the phase separator of about 50%, the upper phase, which comprised about 90% of dimethyl ether and the major part of the excess hydrogen, was pumped continuously back into the hydrogenation reactor and at the same time the inflow of fresh dimethyl ether was reduced to 60 g/h and the amount of fresh hydrogen was reduced to 5 mol/mol of starting material. The lower phase in the phase separator was drained off continuously via a pressure maintenance valve and fractionally distilled according to the prior art. Recovered water was returned to the phase separation.

As hydrogenation product, 1,6-hexanediol was obtained in 96% yield. In addition, 2% of dimeric 1,6-hexanediol and some further by-products in insignificant amounts were found.

Comparative Example 1

Example 1 was repeated but no water was added after the hydrogenation and the temperature in the phase separator was brought down to 50° C. by cooling. No two liquid phases were observed in the phase separator, i.e. the solvent dimethyl ether could not be separated off and recirculated in a simple manner.

Example 2

An oil-heated double-walled tube reactor (3 cm internal diameter) was charged with 10 ml of a Co/Mn catalyst (32% of CoO, 58% of Co, 10% of $Mn_2O_3$) in the form of 0.1 mm shaped bodies. The catalyst was activated firstly using nitrogen/hydrogen mixtures, later using pure hydrogen, at 280° C. and 250 bar. At 150° C. and 250 bar, 5 g/h of adiponitrile, 95 g/h of n-butane and 15 mol of hydrogen per mol of starting material were pumped via a heated helical tube over the catalyst. The hydrogenation output had a temperature of 160° C. and traveled via a cooled mixing section upstream of which 50 g/h of water (25° C.) were introduced to a phase separator having a volume of 2 l. The temperature in the phase separator was 50° C. and the pressure was 250 bar. At a fill level of the phase separator of about 50%, the upper phase, which comprised over 95% of n-butane and the major part of the excess hydrogen, was pumped continuously back into the hydrogenation reactor and at the same time the inflow of fresh n-butane was reduced to 1 g/h and the amount of fresh hydrogen was reduced to 5 mol/mol of starting material. The lower phase in the phase separator was drained off continuously via a pressure maintenance valve. Only very small amounts of hydrogen and n-butane were given off as gases. The remaining product was purified by distillation according to the prior art. Recovered water was returned to the phase separation.

As hydrogenation product, 1,6-diaminohexane was obtained in 85% yield. Furthermore, 5% of dimeric 1,6-diaminohexane, 3% of 1-azacycloheptane and some further by-products in insignificant amounts were found.

Comparative Example 2

Example 2 was repeated but no water was added after the hydrogenation and the temperature in the phase separator was likewise brought down to about 50° C. by cooling. No two liquid phases were observed in the phase separator, i.e. the solvent n-butane could not be separated off and recirculated in a simple manner.

Example 3

The reactor described in example 1 and the same catalyst were used. Here, 9 g/h of maleic anhydride (melt), 81 g/h of n-butane and 10 mol of hydrogen per mol of starting material were pumped via a heated helical tube over the catalyst at 220° C. and 250 bar.

The hydrogenation output had a temperature of 240° C. and traveled via a cooled mixing section upstream of which 100 g/h of water (25° C.) were introduced to a phase separator having a volume of 2 l. The temperature in the phase separator was 50° C. and the pressure was 250 bar. At a fill level of the phase separator of about 50%, the upper phase, which comprised over 95% of n-butane and the major part of the excess hydrogen, was pumped continuously back into the hydrogenation reactor and at the same time the inflow of fresh n-butane was reduced to 2 g/h and the amount of fresh hydrogen was reduced to 6 mol/mol of starting material.

The lower phase in the phase separator was drained off continuously via a pressure maintenance valve. Only very small amounts of hydrogen and n-butane were given off as gas. The remaining product was purified by distillation according to the prior art. Recovered water was returned to the phase separation.

As hydrogenation product, 1,4-butanediol was obtained in 85% yield. Furthermore, 8% of tetrahydrofuran, 5% of gamma-butyrolactone and some further by-products in insignificant amounts were found.

Comparative Example 3

Example 3 was repeated but no water was added after the hydrogenation and the temperature in the phase separator was likewise brought down to about 50° C. by cooling. 2 liquid phases could be seen in the phase separator, but the solubility of butane in the product phase was so high that a major part of the butane was lost via the product phase and 50 g/h of fresh butane had to be introduced to maintain a stable equilibrium, despite recirculation of the butane phase.

The invention claimed is:

1. A process for separating off solvents from solvent-containing hydrogenation outputs from a heterogeneous catalytic hydrogenation process, which comprise at least one water-soluble hydrogenation product having at least one functional group selected from the group consisting of an alcohol, a lactone group, an ether group, a lactam group and an amino group in a solvent which is immiscible or not completely miscible with water and has a boiling point below 100° C., comprising adding water to the hydrogenation output, separating off the solvent-containing phase and recirculating to the hydrogenation.

2. The process according to claim 1, wherein the water-soluble hydrogenation product is selected from the group consisting of methanol, ethanol, propanol, butanol, isobutanol, ethylene glycol, 1,2-propylene glycol and 1,3-butanediol, 1,4-butanediol, 1,2,4-butanetriol, tetrahydrofuran, 2-methyltetrahydrofuran, 3-methyltetrahydrofuran, optionally methyl-substituted gamma-butyrolactone, 1,5-pentanediol, 1,6-hexanediol, 1,4-pentanediol, 2,5-bis(hydroxymethyl)tetrahydrofuran, 1,12-dodecanediol, pyrrolidone, N-alkylpyrrolidones, C-alkylated pyrrolidones, C- and N-alkylated pyrrolidones, N-alkylated monoamines and diamines and amino alcohols and mixtures thereof.

3. The process according to claim 1, wherein the water-soluble hydrogenation product is selected from the group consisting of 1,4-butanediol, tetrahydrofuran, optionally methyl-substituted gamma-butyrolactone, 1,5-pentanediol, 1,6-hexanediol, 1,4-pentanediol, 2,5-bis(hydroxymethyl)tetrahydrofuran, pyrrolidone, N-alkylpyrrolidones, C-alkylated pyrrolidones, C- and N-alkylated pyrrolidones and amino alcohols and mixtures thereof.

4. The process according to claim 1, wherein from 0.01 to 1000% by weight of water, based on the hydrogenation output, are added after the hydrogenation.

5. The process according to claim 1, wherein the phase separation is carried out at temperatures below the hydrogenation output temperature.

6. The process according to claim 1, wherein the phase separation is carried out at temperatures which are from 5 to 250° C. below the hydrogenation output temperature.

7. The process according to claim 1, wherein the phase separation is carried out at temperatures which correspond to the hydrogenation output temperature.

8. The process according to claim 1, wherein the phase separation is carried out at the pressure at which the hydrogenation is also carried out or up to 50 bar below this.

9. The process according to claim 1, wherein the solvent is selected from the group consisting of carbon dioxide, argon, nitrogen, hydrocarbons such as methane, ethane, propane, butane, isobutane, pentane and its isomers, cyclopentane, hexane and its isomers, cyclohexane, heptane and its isomers, aromatics such as benzene, toluene, ethers such as dimethyl ether, methyl ethyl ether, diethyl ether, dipropyl ether, methyl propyl ether, methyl isopropyl ether, ethyl propyl ether, ethyl isopropyl ether, dibutyl ether, methyl-tert-butyl ether, methyl n-butyl or isobutyl ether, ethyl n-butyl or isobutyl ether, propyl n-butyl or isobutyl ether, and isopropyl n-butyl or isobutyl ether.

10. The process according to claim 1, wherein the solvent is selected from the group consisting of carbon dioxide, argon, nitrogen, propane, butane and its isomers, isobutane, pentane and its isomers, dimethyl ether and diethyl ether.

11. The process according to claim 1, wherein the weight ratio of solvent to hydrogenation product is from 0.1 to 1000.

12. The process according to claim 1, wherein the process for separating off solvents is operated continuously together with the preceding catalytic hydrogenation.

13. A process, comprising:
hydrogenating a raw material in one or more solvents in a reactor in the presence of one or more heterogeneous catalysts to form a hydrogenation output comprising at least one water-soluble hydrogenation product having at least one functional group selected from the group consisting of an alcohol group, a lactone group, an ether group, a lactam group and an amino group; wherein the solvent is immiscible or only partially miscible with water and has a boiling point below 100° C.,
mixing water with the hydrogenation output to form a phase-separated output having an aqueous phase and a solvent phase,
separating the solvent phase from the aqueous phase, and recirculating the solvent phase to add the solvent phase to the reactor of the hydrogenating.

14. The process according to claim 13, wherein the hydrogenation product comprises at least one selected from the group consisting of methanol, ethanol, propanol, butanol, isobutanol, ethylene glycol, 1,2-propylene glycol, 1,3-butanediol, 1,4-butanediol, 1,2,4-butanetriol, tetrahydrofuran, 2-methyltetrahydrofuran, 3-methyltetra -hydrofuran, gamma-butyrolactone, methyl-substituted gamma-butyrolactone, 1,5-pentanediol, 1,6-hexanediol, 1,4-pentanediol, 2,5-bis(hydroxymethyl)tetrahydrofuran, 1,12-dodecanediol, pyrrolidone, an N-alkylpyrrolidone, a C-alkylated pyrrolidone, a C- alkylated pyrrolidone, an N-alkylated pyrrolidone, an N-alkylated monoamines, an N-alkylated diamines and an amino alcohol.

15. The process according to claim 13, wherein the water-soluble hydrogenation product is at least one selected from the group consisting of 1,4-butanediol, tetrahydrofuran, gamma-butyrolactone, methyl-substituted gamma-butyrolactone, 1,5-pentanediol, 1,6-hexanediol, 1,4-pentanediol, 2,5-bis(hydroxymethyl)tetrahydrofuran, pyrrolidone, an N-alkylpyrrolidone, a C-alkylated pyrrolidone, a C- alkylated pyrrolidone, an N-alkylated pyrrolidone, and an amino alcohol.

16. The process according to claim 13, wherein from 0.01 to 1,000% by weight of water is added to the hydrogenation output during the mixing, wherein % by weight is based on the weight of the hydrogenation output.

17. The process according to claim 13, further comprising cooling the phase-separated output before the separating.

18. The process according to claim 13, wherein the temperature of the solvent phase is from 5 to 250° C. below the temperature of the hydrogenation output formed in the hydrogenating.

19. The process according to claim 13, wherein the temperature of the aqueous and solvent phases is substantially the same as the temperature of the hydrogenation output.

20. The process according to claim 13, wherein the separating is carried out at the same pressure at which the hydrogenating is carried out or the separating is carried out at a pressure of up to 50 bar below the pressure at which the hydrogenating is carried out.

21. The process according to claim 13, wherein the solvent is at least one selected from the group consisting of carbon dioxide, argon, nitrogen, a hydrocarbon, methane, ethane, propane, butane, isobutane, pentane, an isomers of pentane, cyclopentane, hexane, an isomer of hexane, cyclohexane, heptane, an isomer of heptane, an aromatic, benzene, toluene, an ether, dimethyl ether, methyl ethyl ether, diethyl ether, dipropyl ether, methyl propyl ether, methyl isopropyl ether, ethyl propyl ether, ethyl isopropyl ether, dibutyl ether, methyl-tert-butyl ether, methyl n-butyl or isobutyl ether, ethyl n-butyl ether, isobutyl ether, propyl n-butyl ether, isobutyl ether, isopropyl n-butyl and isobutyl ether.

22. The process according to claim 13, wherein the solvent is at least one selected from the group consisting of carbon dioxide, argon, nitrogen, propane, butane, an isomer of butane, isobutane, pentane, an isomer of pentane, dimethyl ether and diethyl ether.

23. The process according to claim 13, wherein the weight ratio of the solvent to the hydrogenation product formed by the hydrogenating is from 0.1 to 1000.

24. The process according to claim 23, wherein the separating is carried out concurrently with the hydrogenating.

25. The process according to claim 1, wherein hydrogenation product is dissolved in the solvent and the addition of the water forms an solvent phase and a water phase.

26. The process according to claim 1, wherein the hydrogenation product has at least one functional group selected from the group consisting of a lactone group, an ether group, a lactam group and an amino group.

27. The process according to claim 13, wherein the hydrogenation product has at least one functional group selected from the group consisting of a lactone group, an ether group, a lactam group and an amino group.

28. A process for separating off solvents from solvent-containing hydrogenation outputs from a heterogeneous catalytic hydrogenation process, carried out at a pressure of from 50 to 350 bar, which comprise at least one water-soluble hydrogenation product having at least one alcohol, lactone, ether, lactam or amino group in a solvent which is immiscible or not completely miscible with water and has a boiling point below 100° C., comprising adding water to the hydrogenation output, separating off the solvent-containing phase and recirculating to the hydrogenation, and
wherein the solvent-containing phase is separated-off at a pressure of at or up to 20 bar below the pressure of the hydrogenation process.

29. A process, comprising:
hydrogenating a raw material in one or more solvents in a reactor in the presence of one or more heterogeneous catalysts, at a pressure $H_p$ of from 50 to 350 bar, to form a hydrogenation output comprising at least one water-soluble hydrogenation product having at least one functional group selected from the group consisting of an alcohol group, a lactone group, an ether group, a lactam group and an amino group; wherein the solvent is immiscible or only partially miscible with water and has a boiling point below 100° C.,
mixing water with the hydrogenation output to form a phase-separated output having an aqueous phase and a solvent phase,
separating the solvent phase from the aqueous phase at a pressure of from $H_p - 20$ bar to $H_p$, and
recirculating the solvent phase to add the solvent phase to the reactor of the hydrogenating.

30. The process according to claim 1, wherein the heterogenous catalytic hydrogenation process adds $H_2$ to an unsaturated bond.

31. The process according to claim 13, wherein the hydrogenating adds $H_2$ to an unsaturated bond.

32. The process according to claim 28, wherein the heterogenous catalytic hydrogenation process adds $H_2$ to an unsaturated bond.

33. The process according to claim 29, wherein the hydrogenating adds $H_2$ to an unsaturated bond.

34. The process according to claim 1, wherein the heterogeneous catalytic hydrogenation process is carried out with a supported heterogeneous catalyst.

35. The process according to claim 13, wherein the heterogeneous catalyst is a supported heterogeneous catalyst.

36. The process according to claim 28, wherein the heterogeneous catalytic hydrogenation process is carried out with a supported heterogeneous catalyst.

37. The process according to claim 29, wherein the heterogeneous catalyst is a supported heterogeneous catalyst.

* * * * *